United States Patent [19]

Tomiyama et al.

[11] Patent Number: 5,081,152
[45] Date of Patent: Jan. 14, 1992

[54] AZULENE DERIVATIVES AS THROMBOXANE $A_2$ AND PROSTAGLANDIN ENDOPEROXIDE RECEPTOR ANTAGONIST

[75] Inventors: Tsuyoshi Tomiyama; Akira Tomiyama; Masayuki Yokota, all of Sakaki; Shuuichi Wakabayashi, Koushoku; Hiromi Hayashi, Sakaki; Rei Koyama, Kitamimaki; Masafumi Yasunami, Sendai, all of Japan

[73] Assignee: Kotobuki Seiyaku Co., Ltd., Sakaki, Japan

[21] Appl. No.: 544,340

[22] Filed: Jun. 26, 1990

[30] Foreign Application Priority Data

Jul. 5, 1989 [JP] Japan .................................. 1-171953

[51] Int. Cl.$^5$ .................... A61K 31/185; C07C 309/26
[52] U.S. Cl. ........................ 514/577; 562/100
[58] Field of Search ................ 562/100; 514/577, 553

[56] References Cited

U.S. PATENT DOCUMENTS 4,595,694  6/1986  Takase et al. ...................... 562/100

Primary Examiner—Robert W. Ramsuer
Assistant Examiner—Michael G. Ambrose
Attorney, Agent, or Firm—Morrison Law Firm

[57] ABSTRACT

A series of new azulene analogues are disclosed, which are represented by the following formula:

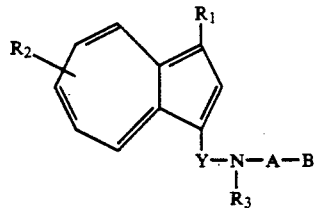

wherein:
$R_1$ is —COOH, —COOR$_4$ ($R_4$ represents a lower alkyl), —CH=CH—COOH, —CH$_2$—COOH or —SO$_3$H;
$R_2$ is a hydrogen atom or lower-alkyl group;
$R_3$ is a hydrogen atom, a lower alkyl or benzyl group;
A is —SO$_2$—,

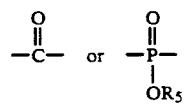

($R_5$ represents a lower alkyl);
B is a phenyl, a lower alkylphenyl, a lower alkoxyphenyl, nitrophenyl, trifluoroalkylphenyl, mono-or dihalogenated-phenyl, naphthyl or tetrahydroaphthyl group;
Y is an alkylene or alkenylene group.

The compounds of the present invention are useful as thromboxane $A_2$ and prostagrandin endoperoxide receptor antagonists.

4 Claims, No Drawings

AZULENE DERIVATIVES AS THROMBOXANE A₂ AND PROSTAGLANDIN ENDOPEROXIDE RECEPTOR ANTAGONIST

BACKGROUND OF THE INVENTION

This invention relates to new azulene derivatives, therapeutic compositions containing these derivatives and the method of manufacturing the same.

Recently, prostaglandins and thromboxane $A_2$, derived from arachidonic acid, are thought to be important mediator of many various diseases such an cardiovascular diseases, inflammatories and etc. Two approaches, are considered to protect patient from the attack of these active mediators.

As the first approach, inhibitors of thromboxane synthetase which synthetizes thromboxane $A_2$ in vivo, will be applied for remedies. In case thromboxane synthetase inhibitors are treated, Allan M. Lefer (Drugs of Today 21,283 291 (1985)) had reported that it is difficult to obtain enough lower plasma level of thromboxane inhibitors to exhibit the therapeutic effect. Fundamentally thromboxane inhibitors have the defect that could not inhibit prostagrandine endoperoxides considered another important mediator.

And as the second approach, the usefulness of thromboxane receptor antagonists are presently explored. These antagonists are classified into prostanoidal and non-prostanoidal antagonists. The later antagonists are known to resist metabolic inactivation as compared to the former antagonists and have no partial agonistic activities.

SUMMARY OF THE INVENTION

The principal object of the present invention is the provision of novel compounds having thromboxane $A_2$ and prostaglandin endoperoxide receptor antagonistic activities.

Another object of the present invention is the provision of pharmaceutical compositions useful as antinephritic agents.

Still other object of the present invention is the provision of new azulene derivatives and a method of the manufacture thereof.

These and other objects of the invention will become apparent from the description that follows hereinafter.

DETAILED DESCRIPTION OF THE INVENTION

This invention relates to a series of new azulene derivatives which are specific and competitive thromboxane $A_2$ and prostaglandin endoperoxide receptor antagonist. These compounds are confirmed as new non-prostanoidal receptor antagonist.

The compounds of the present invention have the following general formula (1)

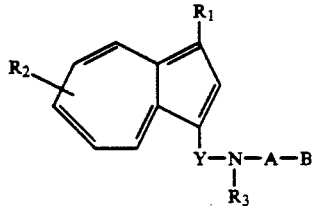

(1)

wherein:

$R_1$ is —COOH, —COOR₄ (R₄ represents a lower alkyl), —CH=CH—COOH, —CH₂COOH or —SO₃H;

$R_2$ is a hydrogen atom or isopropyl group;

$R_3$ is a hydrogen atom or a lower alkyl or benzyl group;

A is —SO₂—,

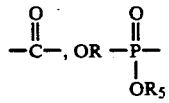

($R_5$ represents a lower alkyl);

B is a phenyl, a lower alkyl phenyl, a lower alkoxyphenyl, nitrophenyl, trifluoroalkylphenyl, mono- or di- halogenated-phenyl, naphthyl or tetrahydronaphthyl group;

Y is a straight-chain or branched-chain alkeylene group of $C_{1\sim10}$ or an alkenylene group of $C_{2\sim6}$, and pharmaceutically acceptable alkali salts thereof.

In this invention, a lower alkyl group means straight-chain or branched-chain alkyl group of $C_{1\sim5}$.

Some compounds fallen within the general formula (1) are as follows.

(1) 3-[2-(Benzenesulfonylamino)ethyl]-azulene-1-carboxylic acid.
(2) 3-[3-(Benzenesulfonylamino)propyl]-azulene-1-carboxylic acid.
(3) 3-[4-(Benzenesulfonylamino)butyl]-azulene-1-carboxylic acid.
(4) 3-[5-(Benzenesulfonylamino)pentyl]-azulene-1-carboxylic acid.
(5) 3-[6-(Benzenesulfonylamino)hexyl]-azulene-1-carboxylic acid.
(6) 3-[7-(Benzenesulfonylamino)heptyl]-azulene-1-carboxylic acid.
(7) 3-[8-(Benzenesulfonylamino)octyl]-azulene-1-carbaxylic acid.
(8) 7-Isopropyl-3-[2-(benzenesulfonylamino)ethyl]-azulene-1-carboxylic acid.
(9) 7-Isopropyl-3-[3-(benzenesulfonylamino)propyl]-azulene-1-carboxylic acid.
(10) 7-Isopropyl-3-[4-(benzenesulfonylamino)butyl]-azulene-1-carboxylic acid.
(11) 7-Isopropyl-3-[5-(benzenesulfonylamino)pentyl]-azulene-1-carboxylic acid.
(12) 7-Isopropyl-3-[6-(benzenesulfonylamino)hexyl]-azulene-1-carboxylic acid.
(13) 7-Isopropyl-3-[7-(benzenesulfonylamino)heptyl]-azulene-1-carboxylic acid.
(14) 3-[7-Isopropyl-3-(2-(benzenesulfonylamino)ethyl)-azulene-1-yl]-2-propenoic acid.
(15) 6-Isopropyl-3-[2-(benzenesulfonylamino)ethyl]-azulene-1-carboxylic acid.
(16) 6-Isopropyl-3-[3-(benzenesulfonylamino)propyl]-azulene-1-carboxylic acid.
(17) 6-Isopropyl-3-[4-(benzenesulfonylamino)butyl]-azulene-1-carboxylic acid.
(18) 6-Isopropyl-3-[5-(benzenesulfonylamino)pentyl]-azulene-1-carboxylic acid.
(19) 6-Isopropyl-3-[6-(benzenesulfonylamino)hexyl]-azulene-1-carboxylic acid.
(20) 6-Isopropyl-3-[7-(benzenesulfonylamino)heptyl]-azulene-1-carboxylic acid.
(21) 6-Isopropyl-3-[4-(2-methylbenzenesulfonylamino)butyl]-azulene-1-carboxylic acid.

(22) 6-Isopropyl-3-[4-(4-methylbenzenesulfonylamino)-butyl]-azulene-1-carboxylic acid
(23) 6-Isopropyl-3-[4-(4-methoxybenzenesulfonylamino)butyl]-azulene-1-carboxylic acid
(24) 6-Isopropyl-3-[4-(4-fluorobenzenesulfonylamino)-butyl]-azulene-1-carboxylic acid.
(25) 6-Isopropyl-3-[4-(4-chlorobenzenesulfonylamino)-butyl]-azulene-1-carboxylic acid.
(26) 6-Isopropyl-3-[4-(3,4-dichlorobenzenesulfonylamino)-butyl]-azulene-1-carboxylic acid.
(27) 6-Isopropyl-3-[4-(4-bromobenzenesulfonylamino)-butyl]-azulene-1-carboxylic acid.
(28) 6-Isopropyl-3-[4-(4-iodobenzenesulfonylamino)-butyl]-azulene-1-carboxylic acid.
(29) 6-Isopropyl-3-[4-(2-trifluoromethylbenzenesulfonylamino)butyl]-azulene-1-carboxylic acid.
(30) 6-Isopropyl-3-[4-(3-trifluoromethylbenzenesulfonylamino)butyl]-azulene-1-carboxylic acid.
(31) 6-Isopropyl-3-[4-(4-trifluoromethylbenzenesulfonylamino)butyl]-azulene-1-carboxylic acid.
(32) 6-Isopropyl-3-[4-(4-nitrobenzenesulfonylamino)-butyl]-azulene-1-carboxylic acid.
(33) 2-[6-Isopropyl-3-[4-(benzenesulfonylamino)butyl]-azulene-1-yl]-acetic acid.
(34) 6-Isopropyl-3-[4-(5,6,7,8-tetrahydro-2-naphthylsulfonylamino)butyl]-azulene-1-carboxylic acid.
(35) 6-Isopropyl-3-[4-(2-naphthylsulfonylamino)butyl]-azulene-1-carboxylic acid.
(36) 3-[6-Isopropyl-3-[4-(benzenesulfonylamino)butyl]-azulene-1-yl]-2-propenoic acid
(37) 6-Isopropyl-3-[4-(N-methylbenzenesulfonylamino)butyl]-azulene-1-carboxylic acid.
(38) 6-Isopropyl-3-[4-(N-ethylbenzenesulfonylamino)-butyl]-azulene-1-carboxylic acid.
(39) 6-Isopropyl-3-[4-(N-benzylbenzenesulfonylamino)-butyl]-azulene-1-carboxylic acid.
(40) 6-Isopropyl-3-[4-(O-methylphenylphosphonylamino)butyl]-azulene-1-carboxylic acid.
(41) 6-Isopropyl-3-[4-(benzoylamino)butyl]-azulene-1-carboxylic acid.
(42) 6-Isopropyl-3-[4-(benzenesulfonylamino)butyl]-azulene-1-sulfonic acid sodium salt.
(43) 6-Isopropyl-3-[4-(P-methylbenzenesulfonylamino)-butyl]-azulene-1-sulfonic acid sodium salt.
(44) 6-Isopropyl-3-[4-(P-methoxybenzenesulfonylamino)butyl]-azulene-1-sulfonic acid sodium salt.
(45) 6-Isopropyl-3-[4-(P-trifluoromethylbenzenesulfonylamino)butyl]-azulene-1-sulfoic acid sodium salt.
(46) 6-Isopropyl-3-[4-(P-nitrobenzenesulfonylamino)-butyl]-azulene-1-sulfonic acid sodium salt.
(47) 6-Isopropyl-3-[4-(P-fluorobenzenesulfonylamino)-butyl]-azulene-1-sulfonic acid sodium salt.
(48) 6-Isopropyl-3-[4-(P-chlorobenzenesulfonylamino)-butyl]-azulene-1-sulfonic acid sodium salt.
(49) 6-Isopropyl-3-[4-(3,4-dichlorobenzenesulfonylamino)butyl-azulene-1-sulfonic acid sodium salt.
(50) 6-Isopropyl-3-[4-(P-bromobenzenesulfonylamino)-butyl]-azulene-1-sulfonic acid sodium salt.
(51) 6-Isopropyl-3-[4-(P-iodobenzenesulfonylamino)-butyl]-azulene-1-sulfonic acid sodium salt.
(52) 6-Isopropyl-3-[4-(5,6,7,8-tetrahydro-2-naphthylsulfonylamino)butyl]-azulene-1-sulfonic acid sodium salt.
(53) 6-Isopropyl-3-[4-(2-napohthylsulfonylamino)-butyl]-azulene-1-sulfonic acid sodium salt.
(54) 6-isopropyl-3-[(1R)-methyl-4-(benzenesulfonylamino)butyl]-azulene-1-carbolxylic acid.
(55) 6-isopropyl-3-[(1S)-methyl-4-(benzenesulfonylamino)butyl]-azulene-1-carboxylic acid.
(56) 6-isopropyl-3-[(2S)-methyl-4-(benzenesulfonylamino)butyl]-azulene-1-carboxylic acid.
(57) 6-isopropyl-3-[(2R)-methyl-4-(benzenesulfonylamino)butyl]-azulene-1-carboxylic acid.
(58) 6-isopropyl-3-[(3R)-methyl-4-(benzenesulfonylamino)butyl]-azulene-1-carboxylic acid.
(59) 6-isopropyl-3-[(3S)-methyl-4-(benzenesulfonylamino)butyl]-azulene-1-carboxylic acid.
(60) 6-isopropyl-3-[(3S)-methyl-4-(4-chlorobenzenesulfonylamino)butyl]-azulene-1-carboxylic acid.
(61) 6-isopropyl-3-[(3S)-methyl-4-(4-chlorobenzenesulfonylamino)butyl]-azulene-1-sulfonic acid sodium salt.
(62) 6-isopropyl-3-[(4S)-(benzenesulfonylamino)pentyl]-azulene-1-carboxylic acid.
(63) 6-isopropyl-3-[(4R)-(benzenesulfonylamino)pentyl]-azulene-1-carboxylic acid.
(64) 6-isopropyl-3-[2,2-dimethyl-4-(benzenesulfonylamino)butyl]-azulene-1-carboxylic acid.
(65) 6-isopropyl-3-[3,3-dimethyl-4-(benzenesulfonylamino)butyl]-azulene-1-carboxylic acid.
(66) 6-isopropyl-3-[3,3-dimethyl-4-(chlorobenzenesulfonylamino)butyl]-azulene-1-carboxylic acid.
(67) 6-isopropyl-3-[3,3-dimethyl-4-(chlorobenzenesulfonylamio)butyl]-azulene-1-sulfonic acid sodium salt.
(68) 6-isopropyl-3-[4-(benzenesulfonylamino)-cis-2-butenyl]-azulene-1-carboxylic acid.
(69) 6-isopropyl-3-[4-(benzenesulfonylamino)-trans-2-butenyl]-azulene-1-carboxylic acid.

The above mentioned compounds numbered from 1 to 69 will be referred to herein after, as compound 1, compound 2, ..., compound 69 respectively.

In case of $R_3$ being H in the general formula (1) the compound of the formula (2):

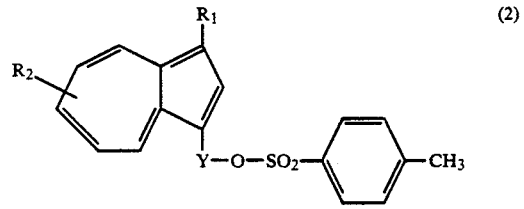

wherein:
$R_1$ is —COOR$_7$, —CH$_2$=CH$_2$COOR$_7$ or —CH$_2$—COOR$_7$ ($R_7$ represents a lower alkyl)
$R_2$, Y are same as mentioned above.
is reacted with the compound of the formula (3):

wherein:
B is same as mentioned above;
and obtained the compound of the formula (4):

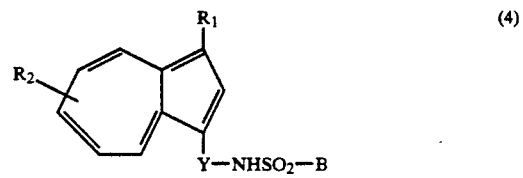

wherein:
$R_1$, $R_2$, B, Y is same as mentioned above.

Furthermore, $R_1$ group of the formula (4) is hydrolyzed and obtained the compound of the general formula (1).

In case of $R_3$ being a lower alkyl or benzyl group in the formula (1), the compound of the formula (4) is reacted with the compound of the formula (5):

$$R_3-X \qquad (5)$$

wherein:

$R_3$ is same as mentioned above;
X is a halogen atom;
and obtained the compound of the formula (6):

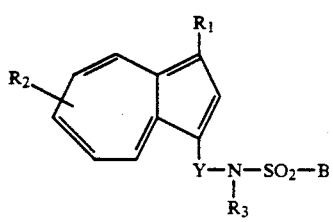
(6)

and the compound of the formula (6) is hydrolyzed if necessary.

The reaction of a compound of the formula (2) and that of the formula (3) can be carried out in the presence of sodium hydride (NaH). A solvent is used in this reaction such as tetrahydrofuran (THF) or hexamethylphosphoramide (HMPA) etc. The reaction proceeds at ambient or elevated temperature. The reaction of a compound of the formula (4) and that of the formula (5) can be carried out in the presence of sodium hydride (NaH) in such an aprotic solvent as dimetylformamide (DMF), dimethylsulfoxide (DMSO) or HMPA.

As alternative method for obtaining the compound of the formula (1) the, Schotten-Bauman reaction is employed. A compound of the formula (7):

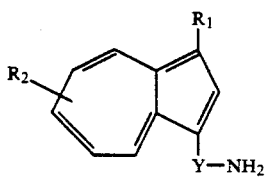
(7)

wherein:

$R_1$, $R_2$ and Y are same as mentioned above,
is reacted with a compound of the formula (8):

$$X-A-B \qquad (8)$$

wherein:

X, A and B are same as mentioned above,
to obtain the compound of the formula (9):

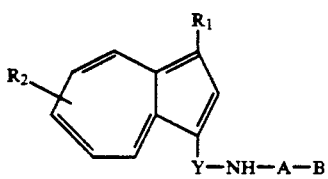
(9)

wherein:

$R_1$, $R_2$, Y, A and B are same as defined before.

Furthermore in case of R being sulfonic acid group in general formula (1), the compound of the formula (10):

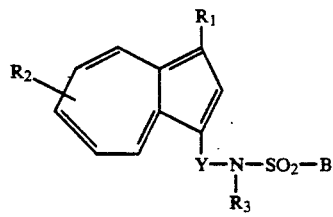
(10)

wherein:

$R_2$, $R_3$, $R_4$ and Y are same as defined before,
is reacted with

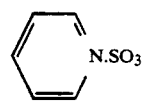

and azulen-sulfonic acid derivative shown in the formula (11) can be obtained.

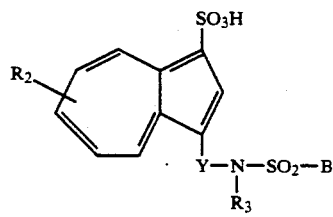
(11)

wherein:

$R_2$, $R_3$, B and n are same as defined before.

In case of $R_1$ being —COOR$_7$ in the formula (2), these compounds can be prepared according to the method described in (Japanese Patent publication, 60-48960) as follows.

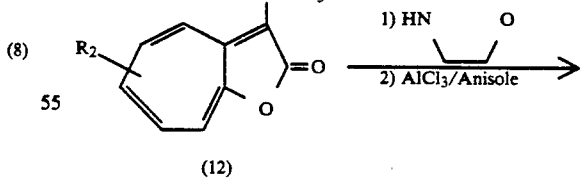
(12)

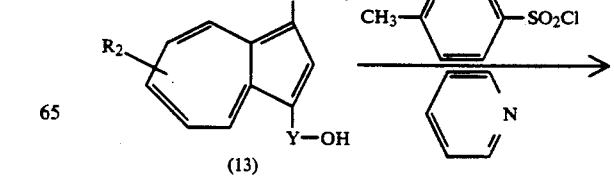
(13)

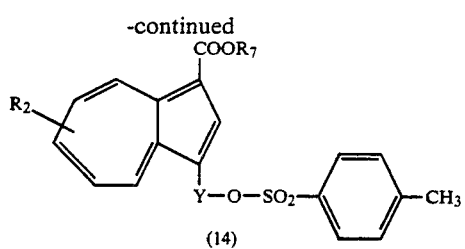

In case of $R_1$ being —CH=CHCOOR$_7$ in the formula (2), the compound of the formula (15) obtained by the above depicted method is carried to Vilsmeier-Haak reaction with POCl$_3$-DMF and can be prepared the compound of the formula (16). The compound of the formula (16) is converted to that of the formula (17) by Horner-Emmons reaction and the compound of the formula (17) can be induced to the compound of the formula (18).

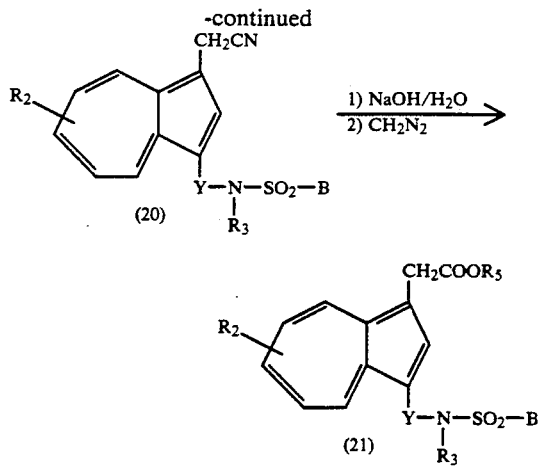

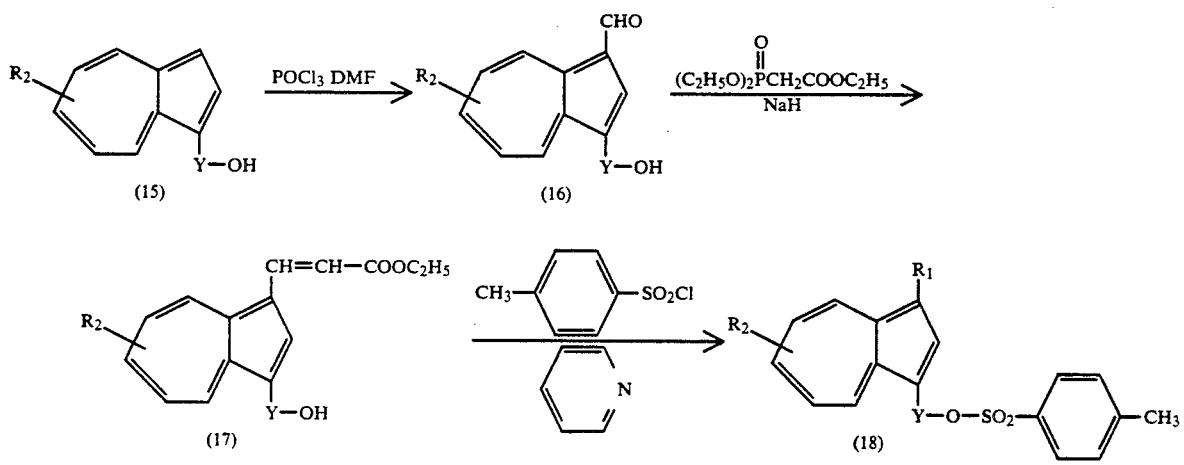

And in case of $R_1$ being —CH$_2$COOR$_2$ in the formula (2), the above described compound of the formula (10) can be induced to the Mannich base shown in the formula (19), followed to react with KCN by the method of E. B. Knott (J. Chem. Soc., 1947, 1190) and can be obtained the compound of the formula (20). After the compound of the formula (20) is hydrolyzed and esterified, the compound of the formula (21) is obtained.

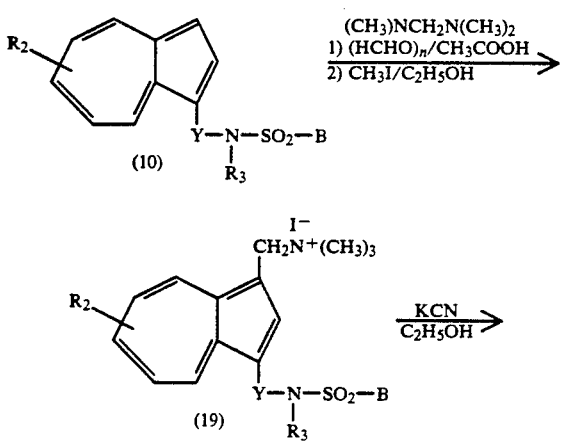

The compounds shown in the formula (15) and the formula (10) can be obtained after de carboxylation of these compounds of general formula (13) with phosphoric acid according to the method described in Japanese patent publication 60-48960.

The reaction products are purified by usually adapted methods such as recrystallization, column chromatograpy etc.

The compounds of the formula (1) of this invention can be applied in the form of free-bases or pharmaceutically acceptable alkali-addition salts, for instance, sodium, potassium, magnesium and calcium salt.

The compounds of the present invention have therapeutic efficacy as thromboxane A$_2$/prostaglandin endoperoxide receptor antagonists for patients with various disorders caused by arachidonic acid metabolites, such as cerebral infarction, myocardial infarction, the other circulatory disorders, arrhythmia, various inflammations, crohn's disease and colitis.

They can be administered orally or parenterally. An effective dosage of the compound is from 1 mg to 300 mg a day for adults, though it may be adjusted depending on symptoms, age and body weight.

Pharmacological experimental examples are as follows.

PHARMACOLOGICAL EXPERIMENT 1

Thromboxane A$_2$ receptor antagonistic action (Inhibitory action of U-46619-induced contractions of rat aortic strips.) Isolated helical strips of rat aorta were mounted vertically, under 1.0 g tension, in organ bath containing 20 ml of krebs-Ringer solution bubbled with a mixture of 95% $O_2$ and 5% $CO_2$.

Inhibitory effects of compounds were examined on rat aortic strip which is precontracted with $3 \times 10^{-8}$M of thromboxane $A_2$ mimetic U-46619, an analogue of thromboxane $A_2$ and prostaglandin endoperoxide.

$IC_{50}$ (the concentrations which inhibited the contraction by 50%) were calculated and shown in table 1.

TABLE 1

| Compd. NO. | $IC_{50}$ (M) |
|---|---|
| 1 | $2.1 \times 10^{-5}$ |
| 3 | $5.7 \times 10^{-7}$ |
| 5 | $1.4 \times 10^{-7}$ |
| 7 | $1.5 \times 10^{-5}$ |
| 10 | $3.1 \times 10^{-6}$ |
| 12 | $9.2 \times 10^{-7}$ |
| 14 | $2.1 \times 10^{-5}$ |
| 15 | $6.0 \times 10^{-5}$ |
| 17 | $7.8 \times 10^{-8}$ |
| 19 | $7.0 \times 10^{-8}$ |
| 22 | $2.0 \times 10^{-8}$ |
| 23 | $1.6 \times 10^{-8}$ |
| 24 | $1.1 \times 10^{-8}$ |
| 25 | $5.3 \times 10^{-9}$ |
| 26 | $4.3 \times 10^{-8}$ |
| 27 | $5.3 \times 10^{-9}$ |
| 28 | $5.1 \times 10^{-9}$ |
| 31 | $1.2 \times 10^{-8}$ |
| 32 | $1.3 \times 10^{-8}$ |
| 33 | $3.0 \times 10^{-7}$ |
| 36 | $2.4 \times 10^{-6}$ |
| 37 | $1.0 \times 10^{-5}$ |
| 41 | $4.4 \times 10^{-6}$ |
| 42 | $1.7 \times 10^{-8}$ |
| 47 | $4.4 \times 10^{-9}$ |
| 48 | $1.7 \times 10^{-9}$ |
| 49 | $1.5 \times 10^{-8}$ |
| 50 | $1.7 \times 10^{-9}$ |
| 51 | $1.6 \times 10^{-9}$ |
| 54 | $2.1 \times 10^{-7}$ |
| 55 | $4.4 \times 10^{-8}$ |
| 56 | $1.6 \times 10^{-7}$ |
| 57 | $3.6 \times 10^{-8}$ |
| 58 | $3.5 \times 10^{-8}$ |
| 59 | $1.6 \times 10^{-8}$ |
| 62 | $5.0 \times 10^{-8}$ |
| 63 | $4.2 \times 10^{-7}$ |
| 64 | $6.9 \times 10^{-7}$ |
| 65 | $5.0 \times 10^{-8}$ |
| 68 | $5.2 \times 10^{-8}$ |
| 69 | $4.6 \times 10^{-7}$ |

REFERENCE EXAMPLE

3-[7-Isopropyl-3-(2-tosyl)ethyl-azulene-1-yl]-2-propenoic acid ethyl ester (1) 7-Isopropyl-3-(2-hydoxy)ethyl-1-formylazulene A $POCl_3$ (0.4 ml) was added to DMF (5.0 ml) at 0° C. and stirred for 10 min. To this mixture, 0.5 g of 7-Isopropyl-[3-(2-hydroxyethyl)]-azulene in DMF (2.5 ml) was added and stirred at 0° C. for 30 min. The mixture was poured into icewater and basified with 10% NaOH solution. The solution was extracted with ethyl acetate. The ethyl acetate extracts were washed with $H_2O$ and brine, dried ($MgSO_4$), then concentrated to dryness. Purification of the residue by silica gel column chromatography (elution with ether) gave 0.556 g of the desired compound (98.1%)

N.M.R. ($CDCl_3$, δ) 10.27 (S,1H), 9.55 (d, 1H), 8.30, 8.41 (d.d,1H), 8.11 (S, 1H), 7.71, 7.82 (d,1H), 7.43, 7.54 (d, 1H), 3.98 (t, 2H), 3.07~3.40 (t+m), 1.96 (b,s, 1H), 1.38, 1.44 (d, 6H)

I.R. (Neat, cm$^{-1}$) 3400, 2930, 2866, 1626, 1530, 1443, 1395, 1365, 1302, 1152, 1041, 804, 753, 705, 651.

M.S. ($^m$/e) 242 (M+), 211 (B.P.), 195, 165, 139, 115, 83, 55.

(2)

3-[7-Isopropyl-3-(2-hydroxy)ethyl-azulene-1-yl]-2-propenoic acid ethyl ester

To a mixture of 0.368 g of NaH in 3.7 ml of tetrahydrofuran (THF), a solution of 2.58 g of ethyl diethylphosphonoacetate in 25.8 ml of THF was added at 0° C. and stirred for 20 min. Then, a solution of 0.556 g of compound obtained from (1) in 5.6 ml of THF was added and the mixture was stirred for 30 min at 0° C. and for 1 hr at room temperature. Saturated $NH_4Cl$ solution was added, the mixture was extracted with ethyl acetate. The extracts were washed with water and brine, dried (MgSO), then concentrated to dryness. Silica gel column chromatography (ethyl acetate: n-hexane (1:1)) of the residue gave 0.400 g (55.7%) of the objective compound.

N.M.R. ($CDCl_3$, δ) 8.43 (d,1H), 8.20, 8.37 (d,1H), 8.19~7.03 (m,4H), 6.30, 6.47 (d,1H,J=15.6 HZ), 4.28 (q,2H), 3.94 (t,2H), 3.25 (t,2H), 2.97~3.36 (m,1H), 1.78 (bs,1H), 1.20~1.50 (dt.t,9H).

I.R. (Neat, cm$^{-1}$) 3448, 2950, 1683, 1602, 1443, 1401, 1368, 1296, 1269, 1215, 1170, 1038, 969, 846, 795, 750.

M.S. ($^m$/e) 317 (M+), 281 (B.P.), 253, 193, 165, 130, 97, 70, 45.

(3)

3-[7-Isopropyl-3-(2-tosyl)ethyl-azulene-1-yl]-2-propenoic acid ethyl ester

To a solution of the compound obtained from (2) in 21.5 ml of pyridine, 1.16 g of P-toluenesulfonylchloride was added and the mixture was stirred for 12 hr at room temperature. The mixture was poured into ice-water and extracted with ethyl acetate. The extracts were washed with water and brine, dried ($MgSO_4$), then evaporated to dryness.

Purification of the residue by chromatography ($SiO_2$, Ether n-hexane (2:1)) gave 1.46 g (65.2%) of oily objective compound.

N.M.R. ($CDCl_3$, δ) 8.39 (d,1H), 8.16, 8.23 (d,1H), 8.02~6.96 (m,9H), 6.12, 6.38 (d,1H,15.6 HZ), 4.08~4.46 (t+q,4H), 3.30 (t,2H), 2.91~3.30 (m,1H), 2.33 (S,3H), 1.20~1.50 (d+t,9H).

I.R. (Neat, cm$^{-1}$) 2956, 1689, 1605, 1446, 1362, 1296, 1269, 1242, 1215, 1173, 1095, 1038, 969, 906, 846, 813, 753, 663.

M.S. ($^m$/e) 466 (M+), 421, 374, 330, 295, 281 (B.P.), 253, 191, 165, 118, 91, 65.

EXAMPLE 1

3-[2-(Benzenesulfonylamino)ethyl]-azulene-1-carboxylic acid (Compound.1)

(1)

3-[2-(Benzenesulfonylamino)ethyl]-azulene-1-carboxylic acid methyl ester

Sodium hydride (60% in oil, 0.503 g) was washed with pentane, and suspended in THF (5 ml). A solution of benzenesulfonamide (2.10 g) in THF (10 ml) was added to the suspension, and the mixture was stirred at 20° C. for 10 min. Then the 3-(2-tosyl oxy) ethyl-azulene-1-carboxylic acid methyl ester (2.50 g) in HMPA (5.0 ml) was dropped into the solution of the sodium salt, and the whole mixture was heated under reflux for 4 hr. The reaction was quenched by the addition of saturated aqueous NH₄Cl, followed by extraction with ethyl acetate. The combined ethyl acetate extracts were washed with water and brine, and dried over MgSO₄. Removal of the solvent and the purification by silica gel column chromatography (chloroform-methanol, 50:1) afforded the sulfonamide (1.30 g, 54%) as a violet crystal.

m.p. 131°~132° C.

N.M.R. (CDCl₃, δ) 9.47, 9.58 (d,1H), 8.21, 8.30 (d,1H), 8.09 (S,1H) 7.13~7.90 (m,7H), 4.67 (bt,1H), 3.91 (S,3H), 3.05~3.52 (m,4H).

I.R. (KBr,cm⁻¹) 3320, 2930, 1677, 1446, 1419, 1332, 1215, 1200, 1161, 740.

M.S. (ᵐ/e) 369 (M⁺), 338, 199 (B.P.), 169, 139, 115, 77, 51.

(2)
3-[2-(Benzenesulfonylamino)ethyl]-azulene-1-carboxylic acid (Compound 1)

A 10% NaOH aqueous solution (9 ml) was added to a solution of the methyl ester (0.9 g) in methanol (18 ml) at room temperature, and the mixture was heated under reflux for 2 hr, followed by evaporation of methanol. The aqueous layers were washed with chloroform. They the aqueous layers were acidified to PH 2-3 with 10% aqueous HCl, followed by extraction with ethyl acetate. The combined organic layers were washed with water and brine, and dried over MgSO₄. Removal of the solvent and the purification by sitica gel column chromatography (ethyl acetate-methanol, 30:1) afforded the carboxylic acid (0.6 g, 70%) as a violet crystal.

m.p. 193°~195° C.

N.M.R. (DMSO, δ) 12.15 (bs,1H), 9.40, 9.51 (d,1H), 8.33, 8.44 (d,1H) 8.13 (S,1H), 7.31~8.02 (m,7H), 3.30 (bs,1H), 2.40~3.23 (m,4H).

I.R. (KBr,cm⁻¹) 3450, 2830, 1638, 1440, 1314, 1236, 1155, 1055, 730.

M.S. (ᵐ/e) 355 (M⁺), 311, 185, 141 (B.P.), 115, 77, 51.

The following compounds are obtained in the same manner as the methods of Example 1.

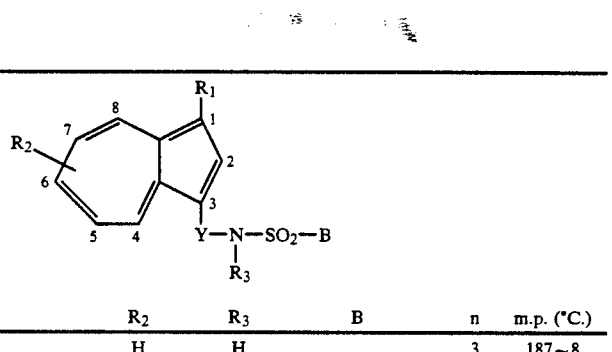

| Compd. No. | R₁ | R₂ | R₃ | B | n | m.p. (°C.) |
|---|---|---|---|---|---|---|
| 2 | —COOH | H | H | ⌬ | 3 | 187~8 |
| 3 | —COOH | H | H | ⌬ | 4 | 168~9 |
| 4 | —COOH | H | H | ⌬ | 5 | 170~1 |
| 5 | —COOH | H | H | ⌬ | 6 | 168~9 |
| 6 | —COOH | H | H | ⌬ | 7 | 143~4 |
| 7 | —COOH | H | H | ⌬ | 8 | 182~4 |
| 8 | —COOH | CH₃\CH—(7)/CH₃ | H | ⌬ | 2 | 166~7 |

-continued
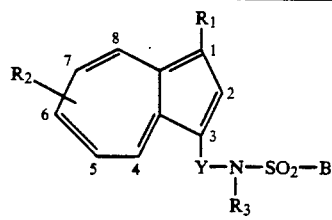
| Compd. No. | R₁ | R₂ | R₃ | B | n | m.p. (°C.) |
|---|---|---|---|---|---|---|
| 9 | —COOH | H | H | phenyl | 3 | 78~80 |
| 10 | —COOH | H | H | phenyl | 4 | 142~3 |
| 11 | —COOH | H | H | phenyl | 5 | 146~7 |
| 12 | —COOH | H | H | phenyl | 6 | 85~8 |
| 13 | —COOH | H | H | phenyl | 7 | 124~5 |
| 14 | —CH=CH—COOH | H | H | phenyl | 2 | 177~8 |
| 15 | —COOH | (CH₃)₂CH— (6) | H | phenyl | 2 | 165~6 |
| 16 | —COOH | (CH₃)₂CH— (6) | H | phenyl | 3 | 120~2 |
| 18 | —COOH | (CH₃)₂CH— (6) | H | phenyl | 5 | 75~6 |
| 19 | —COOH | (CH₃)₂CH— (6) | H | phenyl | 6 | 117~8 |
| 20 | —COOH | (CH₃)₂CH— (6) | H | phenyl | 7 | 119~120 |

-continued
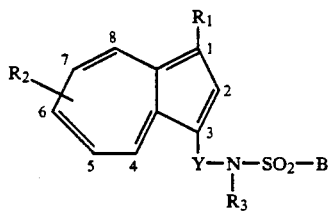
| Compd. No. | R₁ | R₂ | R₃ | B | n | m.p. (°C.) |
|---|---|---|---|---|---|---|
| 21 | —COOH | (CH₃)₂CH— (6) | H | 2-CH₃-phenyl | 4 | 177~8 |
| 22 | —COOH | (CH₃)₂CH— (6) | H | 4-CH₃-phenyl | 4 | 168~9 |
| 23 | —COOH | (CH₃)₂CH— (6) | H | 4-OCH₃-phenyl | 4 | 166~7 |
| 24 | —COOH | (CH₃)₂CH— (6) | H | 4-F-phenyl | 4 | 170~2 |
| 25 | —COOH | (CH₃)₂CH— (6) | H | 4-Cl-phenyl | 4 | 185~6 |
| 26 | —COOH | (CH₃)₂CH— (6) | H | 3,4-diCl-phenyl | 4 | 182~4 |
| 27 | —COOH | (CH₃)₂CH— (6) | H | 4-Br-phenyl | 4 | 191~2 |
| 28 | —COOH | (CH₃)₂CH— (6) | H | 4-I-phenyl | 4 | 186~8 |
| 29 | —COOH | (CH₃)₂CH— (6) | H | 2-CF₃-phenyl | 4 | 120~1 |
| 30 | —COOH | (CH₃)₂CH— (6) | H | 3-CF₃-phenyl | 4 | 168~9 |

-continued

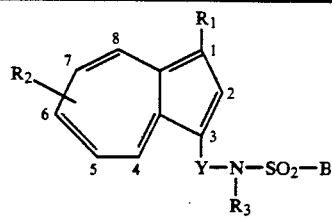

| Compd. No. | R₁ | R₂ | R₃ | B | n | m.p. (°C.) |
|---|---|---|---|---|---|---|
| 31 | —COOH | (CH₃)₂CH— (6) | H | —C₆H₄—CF₃ (para) | 4 | 194~5 |
| 32 | —COOH | (CH₃)₂CH— (6) | H | —C₆H₄—NO₂ (para) | 4 | 171~3 |
| 34 | —COOH | (CH₃)₂CH— (6) | H | tetrahydronaphthyl | 4 | 158~9 |
| 35 | —COOH | (CH₃)₂CH— (6) | H | naphthyl | 4 | 168~9 |
| 36 | —CH=CH—COOH | (CH₃)₂CH— (6) | H | phenyl | 4 | 58~60 |

EXAMPLE 2

6-Isopropyl-3-[4-(benzenesulfonylamino)butyl]-azulene-1-carboxylic acid (Compound 17)

(1)

6-Isopropyl-3-[4-(benzenesulfonylamino)butyl]-azulene-1-carboxylic acid methyl ester NaHCO₃ (0.047 g) in water (1.5 ml) and benzenesulfonylchloride (0.08 ml) in acetone (1.5 ml) were mutually added to a solution of the 6-Isopropyl-3-(4-amino)-butyl-azulene-1-carboxylic acid methyl ester(0.15 g) in acetone (3.0 ml) at 0° C. and the mixture as stirred at the same temperature for 1 hr, followed by evaporation of acetone. The aqueous layers were extracted with ethyl acetate. The combined ethyl acetate extracts were washed with water and brine, and dried over MgSO₄. Removal of the solvent and the purification by silica gel column chromatography (ethyl acetate-n-hexane, 1:2) afforded the sulfonamide (0.15 g, 68.2%) as a violet oil.

N.M.R. (CDCl₃, δ) 9.37, 9.49 (d,1H), 8.16, 8.28 (d,1H), 8.00 (S,1H) 7.17~7.89 (m, 7H), 4.69 (bt,1H), 3.90 (S,3H), 2.80~3.27 (m+2t,5H), 1.20~1.93 (m,4H), 1.31, 1.39 (d,6H).

I.R. (Neat, cm⁻¹) 3320, 3010, 1677, 1449, 1423, 1326, 1215, 1158, 756, 669.

M.S. (m/e) 440 (M+), 439 (M+1), 408, 298, 266, 241 (B.P.), 195, 165, 141, 77, 51.

(2)

6-Isopropyl-3-[4-(benzenesulfonylamino)butyl]-azulene-1-carboxylic acid (Compound 17)

A 10% NaOH aqueous solution (11 ml) was added to a solution of the methyl ester (1.1 g) in methanol(10 ml) at room temperature, and the mixture was heated under reflux for 4 hr, followed by evaporation of methanol. The aqueous layers was washed with chloroform. Then, the aqueous layers was acidified to PH 3-4 with 10% aqueous HCl, followed by extraction with ethyl acetate. The combined organic layers were washed with water and brine, and dried over MgSO₄. Removal of the solvent and purification by silica gel column chromatography (ethyl acetate-n-hexane, 2:1) afforded the carboxylic acid (0.89 g, 84%) as a violet crystal.

m.p. 167°~168° C.

N.M.R. (D6-DMSO,δ) 12.01 (bs,1H), 9.30, 9.42 (d,1H), 8.32, 8.44 (d,1H), 7.98 (S,1H), 7.31~7.84 (m,7H), 3.30 (bt,1H), 2.62~3.40 (m+2t,5H), 1.20~1.80 (m,4H), 1.29, 1.38 (d,6H).

I.R. (KBr,cm⁻¹) 3274, 2950, 1653, 1581, 1461, 1326, 1248, 1155.

M.S. (m/e) 381 (M+31 44), 223, 183 (B.P.), 141, 115, 77.

The following compounds are obtained in the same manner as the methods of Example 2.

| Compd. No. | | m.p. (°C.) |
|---|---|---|
| 40 | [structure: azulene with COOMe at 1-position, isopropyl, and (CH$_2$)$_4$—NH—P(=O)(OMe)—phenyl at 3-position] | oil |
| 41 | [structure: azulene with COOH at 1-position, isopropyl, and (CH$_2$)$_4$—NH—C(=O)—phenyl at 3-position] | 93~4 |

EXAMPLE 3

2-6-Isopropyl-3-[4-(benzenesulfonylamino)butyl]-azulene-1-acetic acid. (Compound 33)

(1)

6-Isopropyl-3-[4-(benzenesulfonylamino)butyl]-1-cyanomethyl-azulene

A mixture of N,N,N',N'-tetramethyldiaminomethane (0.054 g), paraformaldehyd (0.010 g), and acetic acid (1.0 ml) was heated to develop a clear solution. This solution, cooled to 0° C., was added dropwise with stirring to 6-Isopropyl-3-[4-(benzenesulfonylamino)butyl]-azulene (0.181 g) in CH$_2$Cl$_2$ (10 ml) at 0° C., placed in the refrigerator overnight. The reaction was quenched by the addition of 10% aqueous NaOH, followed by extraction with ethyl acetate. The combined ethyl acetate extracts were washed with water and brine, and dried over MgSO$_4$. Removal of the solvent afforded crude product. Methyl iodide (5 ml) was added to the solution of the crude product in ethanol (10 ml) at room temperature, and the mixture was stirred at the same temperature for 2 hr. Removal of the solvent afforded the crude quaternary iodide. To quaternary ammonium iodide in ethanol (10 ml) was added KCN (0.094 g). The mixture was heated under reflux for 1 hr. The reaction was quenched by the addition of water, followed by extraction with ethyl acetate. The combined ethyl acetate extracts were washed with water and brine, and dried over MgSO$_4$. Removal of the solvent and the purification by silica gel column chromatography (ethyl acetate-n-hexane,1:2) afforded the nitrile (0.13 g, 65%).

N.M.R. (CDCl$_3$, δ) 8.06, 8.17 (d,1H), 7.95, 8.06 (d,1H) 7.27~7.40 (m,6H), 6.96, 7.08 (d,2H), 4.91 (bt.1H), 4.02 (S,2H), 2.70~3.20 (t+g+m,5H), 1.11~1.87 (m,4H) 1.39, 1.46 (d,6H).

I.R. (Neat,cm$^{-1}$) 3274, 2944, 2250, 1578, 1446, 1323, 1155, 1089, 750, 690

M.S. ($^m$/e) 420 (M$^{30}$−1), 262, 222 (B.P.), 193, 167, 141, 77.

(2)

2-6-Isopropyl-3-[4-(benzenesulfonylamino)butyl]-azulene-1-acetic acid (Compound 33)

A 0.6N-KOH aqueous solution (10 ml) was added to a solution of the nitrile (0.11 g) in ethanol (10 ml) at room temperature and the mixture was heated under reflux for 12 hr, followed by evaporation of ethanol. The aqueous layers were washed with chloroform. Then, the aqueous layers were acidified to PH 2-3 with 10% aqueous HCL, followed by extraction with ethyl acetate. The combined organic layers were washed with water and brine, and dried over MgSO$_4$. Removal of the solvent afforded the crude acid, with was treated which ethereal diazo methane. After evaporation, the residue was purified by silica gel column chromatography (ethyl acetate-n-hexane, 1:4) to afford the methylester (0.45 g, 92%) as a violet oil. A 10% aqueous solution (4.5 ml) was added to a solution of the methyl ester (0.45 g) in methanol (10 ml) at 0° C., and the mixture was stirred at the same temperature for 12 hr, followed by evaporation of methanol. The aqueous layers were washed with chloroform. Then, the aqueous layers were acidified to PH 2-3 with aqueous 10% aqueous HCL, followed by extraction with ethyl acetate. The combined organic layers were washed with water and brine, and dried over MgSO$_4$. Removal of the solvent and the purification by silica gel column chromatography (ethyl acetate) afforded the acid (0.40 g, 92%) as a violet crystal.

m.p. 51°~52° C.

N.M.R. (CDCl$_3$, δ) 8.10, 8.25 (d,1H), 7.90, 8.04 (d,1H), 7.28~7.96 (m,6H), 6.86~7.07 (dd,1H), 4.30~4.60 (bt+m,2H), 4.01 (S,2H), 2.77~3.15 (t+g+m,5H), 1.15~1.83 (m,4H), 1.28~1.35 (d,6H).

I.R. (KBr, cm$^{-1}$) 3268, 2944, 1704, 1578, 1446, 1323, 1155, 1092.

M.S. ($^m$/e) 439 (M$^+$−1), 395, 281, 241, 197 (B.P.), 167, 141, 77.

EXAMPLE 4

6-Isopropyl-3-[4-(N-methylbenzenesulfonylamino)butyl]-azulene-1-carboxylic acid (Compound 35)

(1)

6-Isopropyl-3-[4-(N-methylbenzenesulfonylamino)butyl]-azulene-1-carboxylic acid methyl ester sodium hydride (60% in oil, 0.06 g) was washed with pentane, and suspended in DMF (20 ml).

A solution of 6-Isopropyl-3-[4-(benzenesulfonylamino)butyl]-azulene-1-carboxylic acid methyl ester (0.50 g) in DMF (10 ml) was added to the suspension, and the mixture was stirred at 0° C. for 10 min.

Then, methyl iodide (5 ml) was dropped into the solution of the sodium salt, and the mixture was stirred at the same temperature for 30 min. The reaction was quenched by the addition of saturated aqueous NH₄Cl, followed by extraction with ethyl acetate. The combined ethyl acetate extracts were washed with water and brine, and dried over MgSO₄. Removal of the solvent and the purification by silica gel column chromatography (ethyl acetate-n-hexane, 1:1) afforded the sulfonamide (0.51 g 99%) as a violet oil.

N.M.R. (CDCl₃, δ) 9.42, 9.53 (d,1H), 8.28, 8.30 (d,1H), 8.09 (S,1H), 7.65~7.85 (m,2H), 7.25~7.60 (m,5H), 3.93 (S 3H) 2.86~3.20 (m,5H), 2.68 (S 3H), 1.40~1.95 (m,4H) 1.33~1.40 (d 6H).

M.S. (m/e) 453 (M+), 422, 312, 280 (B.P.), 241, 195, 165, 139, 77, 51.

I.R. (Neat, cm⁻¹) 3004, 2920, 854, 1683, 1578, 1446, 1419, 1338, 1209, 1161, (2)

6-Isopropyl-3-[4-(N-methylbenzenesulfonylamino)-butyl]-azulene-1-carboxylic acid (Compound 35)

A 10% KOH aqueous solution (10 ml) was added to a solution of the methyl ester (0.36 g) in ethanol (5 ml) at room temperature, and the mixture was heated under reflux for 4 hr, followed by evaporation of ethanol. The aqueous layers were washed with chloroform. Then, the aqueous layers were acidified to PH 2-3 with 10% aqueous HCl, followed by extraction with ethyl acetate. The combined organic layers were washed with water and brine, and dried over MgSO₄. Removal of the solvent and the purification by silica gel column chromatography (ethyl acetate:n-hexane, 1:1) afforded the carboxylic acid (0.25 g 81%) as a violet crystal.

m.p. 153°~155° C.

N.M.R. 9.48, 9.50 (d,1H), 8.32, 8.43 (d,1H), 8.18 (S,1H), 7.60~7.85 (m,2H), 7.26~7.60 (m+bs,6H), 2.80~3.25 (m,5H), 2.70 (S,3H) 1.50~1.95 (m,4H), 1.34~1.42 (d,6H).

M.S. (m/e) 439 (M+), 395, 254, 223, 183, (B.P.), 153, 115, 77.

I.R. (KBr, cm⁻¹) 2914, 1632, 1455, 1431, 1335, 1236, 1155, 723.

The following compounds are obtained in the same manner as the method of Example 4.

EXAMPLE 5

6-Isopropyl-3-[4-(benzenesulfonylamino)butyl]-azulene-1-sulfonic acid sodium salt (compound 42)

(1)

6-Isopropyl-3-[4-(benzenesulfonylamino)butyl]-azulene

A solution of 6-Isopropyl-3-[4-(benzenesulfonylamino)butyl]-azulene-1-carboxylic acid methyl ester (1.53 g) in 100% phosphoric acid (13 ml) was stirred at 120° C. for 20 min. The reaction mixture was poured on ice-water, and extracted with ethyl acetate. The ethyl acetate extracts were washed with water and dried over MgSO₄. Removal of the solvent and the purification by silica gel columnchromatography (ethyl acetate-n-hexane, 1:3) afforded the title compound (1.23 g 94%) as a violet crystal 75°~76° C.

N.M.R. (CDCl₃, δ) 8.11~8.24 (d,1H), 7.90~8.10 (d,1H), 7.11~7.90 (m, 7H), 6.92, 7.04 (d,2H), 4.35 (b.t.,1H), 2.76~3.20 (t+g+m,5H), 1.20~1.93 (m,4H), 1.29, 1.37 (d,6H).

I.R. (KBr, cm⁻¹) 3262, 2920, 1575, 1446, 1326, 1152, 1062, 837.

M.S. (m/e) 381 (M³⁰), 223, 183 (base), 141, 115, 77, 51.

(2)

6-Isopropyl-3-[4-(benzenesulfonylamino)butyl]-azulene-1-sulfonic acid sodium salt (Compound 42)

SO₃.pyridine complex (0.42 g) was added to the solution of azulene (0.50 g) in benzene (10 ml) at room temperature, and the mixture was heated under reflux for 12 hr, followed by evaporation of solvent. The residue was washed with ether, treated with sodium methoxide (10% NaOMe in MeOH, 0.25 ml) in MeOH (10 ml) for 2.4 hr, followed by evaporation of methanol. The residue was added water, and extracted with THF. The combined organic layers were dried over MgSO₄. Removal of the solvent and the purification by silica gel column chromatography (chloroform-methanol; 10:1) afforded the sulfonic acid sodium salt (0.46 g 73%) as a violet crystal.

m.p. 207°~208° C.

N.M.R. (CD₃OD,δ) 8.94, 9.06 (d,1H), 8.24, 8.36 (d,1H), 7.40~7.90 (m,6H), 7.20~7.31 (d,2H), 2.75~3.04 (t+g+m, 5H), 1.20~1.79 (m,4H), 1.31~1.39 (d,6H).

I.R. (KBr, cm⁻¹) 3268, 2944, 1578, 1446, 1401, 1323, 1155, 1092, 1038, 639.

The following compounds are obtained in the same manner as the methods of Example 5.

| Compd. No. | | m.p. (°C.) |
|---|---|---|
| 38 | COOH, isopropyl-azulene with (CH₂)₄—NHSO₂—phenyl, C₂H₅ | 148~151 |
| 39 | COOH, isopropyl-azulene with (CH₂)₄—N(CH₂-phenyl)—SO₂—phenyl | 61~63 |

SO₃Na, isopropyl-azulene with (CH₂)₄—NHSO₂—B

| Compd. No. | B | m.p. (°C.) |
|---|---|---|
| 43 | —phenyl—CH₃ | 198-199 |

-continued

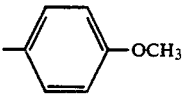

| Compd. No. | B | m.p. (°C.) |
|---|---|---|
| 44 | 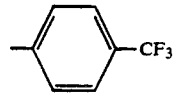 | 205-206 |
| 45 | 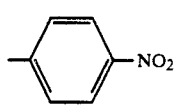 | 181-182 |
| 46 | 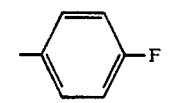 | 205-206 |
| 47 | 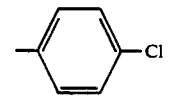 | 197-208 |
| 48 | 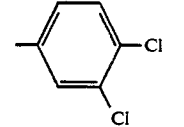 | 201-202 |
| 49 | 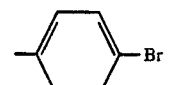 | 197-199 |
| 50 | 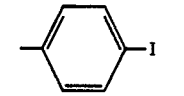 | 199-200 |
| 51 | 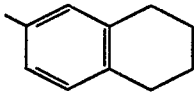 | 200-201 |
| 52 | 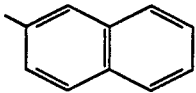 | 195-196 |
| 53 |  | 199-201 |

EXAMPLE 6

6-isopropyl-3-[(3S)-methyl-4-(4-chlorobenzenesulfonylamino)butyl]azulene-1-carboxylic acid
(Compound 60)

(1) (2S)-Methyl-3-tetrahydropyranyloxy-1-propanol

A mixture of (S)-(+)-methyl-3-hydroxy-2-methylpropionate (10.0 g), 2,3-dihydropyran (10.0 g) and D,L-10-camphorsulfonic acid in $CH_2Cl_2$ (200 ml) was stirred for 30 min at room temperature. The reaction was quenched by the addition of saturated aqueous NaHCO$_3$, followed by extraction with ether. The combined extracts were washed with water, dried over MgSO$_4$ and concentrated to give 17.1 g of crude product. A solution of crude product (17.1 g) in ether (30 ml) was added dropwise during 40 min to a stirred and ice cooled suspension of LiAlH$_4$ (3.21 g) in dry ether (300 ml). The stirring was continued for 30 min at room temperature. The excess LiAlH$_4$ was decomposed by the successive addition of water (8 ml), 15% NaOH (8 ml) and water (24 ml) and the stirred and ice-cooled mixture was filtered. The filtrate was dried over MgSO$_4$ and concentrated in vacuo. The residue was distilled to give 14.6 g of (1). b.p. 85 89/3.5 mmHg.

$^1$H-NMR δ (CDCl$_3$) 0.89, 0.96 (3H,d), 1.07~2.26 (7H,m), 2.50~2.76 (1H,m), 3.20~4.08 (6H,m), 4.54 (b.s,1H,).

(2) (2S)-methyl-3-tetrahydropyranyloxypropyl tosylate p-TsCl (19.2 g) was added portionwise during 5 min to a solution of (1) (14.6 g) in pyridine (146 ml) with stirring and ice-cooling. The mixture was stirred at 3° for 15 hr, the mixture was poured into ice-water and extracted with ether. The ether solution was washed with cooled 0.5N aqueous HCl, saturated aqueous CuSO$_4$; water, saturated aqueous NaHCO$_3$ and brine, dried over MgSO$_4$ and concentrated to give 27.5 g of (2).

(3) (2S)-methyl-3-phenylthio-1-propanol tetrahydropyranyl ether

A solution of (2) (27.5 g) in EtOH (46 ml) was added dropwise during 10 min to a solution of PhSNa prepared from PhSH (11.2 ml) and Na (3.01 g) in EtOH (130 ml) with stirring at room temperature. The mixture was stirred and heated under reflux for 2.5 hr. The mixture was poured into iced 2N aqueous NaOH and extracted with ether. The ether solution was washed with brine, dried over MgSO$_4$ and concentrated in vacuo to give 22.3 g of (3).

(4) (2S)-methyl-3-phenysulfonyl-1-propanol tetrahydropyranyl ether

NaHCO$_3$ (19.2 g) was added to a stirred solution of (3) (22.3 g) in $CH_2Cl_2$ (720 ml) and the mixture was cooled to −25°. To this mixture was added with stirring and MCPBA (44.6 g) during 40 min at −25° to −15°. The mixture was stirred for 15 hr room temperature. It was then washed with saturated aqueous NaHCO$_3$ and brine, dried over MgSO$_4$ and concentrated in vacuo. The residue was chromatographed on SiO$_2$. Elution with n-hexane-ether (1:1) gave 21.7 g of (4)

$^1$H-NMR δ (CDCl$_3$) 1.06, 1.13 (6H,d), 1.20~1.90 (6H,m), 2.09~2.51 (1H,m), 2.69~3.83 (6H,m), 4.30~4.52 (1H,m), 7.20~8.00 (5H,m).

(5) (2S)-methyl-3-phenylsulfonyl-5-hexane-1-ol tetrahydropyranyl ether

A solution of n-BuLi in hexane (1.6M, 46.0 ml) was added dropwise during 15 min to a stirred and cooled solution of (4) (20.0 g) in THF (200 ml) at −78°. The mixture was stirred for 25 min at −78°. Then HMPA (15.0 ml) was added dropwise during 3 min at −78. The stirring was continued for 10 min. A solution of allyl iodide (14.6 g) in THF (40 ml) was added to the stirred and cooled mixture during 15 min at −78°. The mixture was stirred for 4 hr at −78°. The reaction was quenched by the addition of saturated aqueous NH$_4$Cl, followed by extraction with ether. The combined ether extracts were washed with water and brine, dried over MgSO$_4$, and concentrated in vacuo. The residue was chromatographed on SiO$_2$. Elution with n-hexane ether (3:1) gave 20.0 g of (5)

$^1$H-NMR δ (CDCl$_3$) 0.91~1.10 (3H,2d), 0.90~1.88 (6H,m), 2.20~2.75 (4H,m), 3.03~4.16 (4H,m), 4.30~4.53 (1H,m), 4.75~5.17 (2H,m), 5.30~5.81 (1H,m), 7.30~8.00 (5H,m).

(6) (2S)-methyl-5-hexane-1-ol tetrahydropyranyl ether

A solution of (5) (1.2 g) in EtOH (20 ml) was added dropwise during 15 min to 5% Na-Hg (7.0 g) with stirring for 1 hr at room temperature. The mixture was stirred and heated under reflux for 3 hr. The mixture was filtered and filtrate was concentrated in vacuo. The residue was diluted with ether. The ether solution was washed with saturated aqueous NH$_4$Cl and brine, dried over MgSO$_4$, and concentrated in vacuo. The residue was chromatographed on SiO$_2$. Elution with n-hexane-ether (1:4) gave 0.54 g of (6).

$^1$H-NMR δ (CDCl$_3$) 0.91, 0.99 (3H,d), 0.63~2.28 (11H,m), 3.02~4.01 (4H,m), 4.56 (1H,b.s), 4.72~5.14 (2H,m), 5.53~6.07 (1H,m)

(7) (5S)-methyl-6-tetrahydropyranyloxy-1-hexanol

9-BBN (0.5M, solution in THF, 7.5 ml) was added to a solution of (6) in THF (7.5 ml), and the mixture was stirred for 2 hr at room temperature. Then, 6N aqueous NaOH (3.6 ml) and 30% H$_2$O$_2$ (1.6 ml) were added, and the whole reaction mixture was stirred at 60° for 2 hr. After separation of THF, the reaction mixture was extracted with ether. The combined organic layers were washed with aqueous Na$_2$S$_2$O$_3$ and brine, dried over MgSO$_4$ and concentrated in vacuo. The residue was chromatographed on SiO$_2$. Elution with n-hexane-ether (1:2) gave 0.42 g of (7)

$^1$H-NMR δ (CDCl$_3$) 0.89, 0.96 (3H,d), 0.60~2.00 (12H,m), 3.00~4.03 (6H,m), 4.53 (1H,b.s).

(8) (5S)-methyl-6-tetrahydropyranyloxy-1-hexanol

AcONa (0.3 g) and PCC (14.2 g) were added to a solution of (7) (1.4 g) in CH$_2$Cl$_2$ (30 ml) at 0° C. and mixture was stirred for 2 hr. After dilution with ether, the reaction mixture was filtered through a SiO$_2$ column. The filtrate was concentrated to give 1.0 g of (8)

$^1$H-NMR δ (CDCl$_3$) 0.90, 0.98 (3H,d), 1.05~2.03 (11H,m), 2.43 (2H,dtt), 3.20~4.07 (4H,m), 4.53 (1H,b.s), 9.74 (1H,t).

(9) 6-Isopropyl-3-[(3S)-methyl-4-tetrahydropyranyloxy)-1-butyl]-azulene-1-carboxylic acid methyl ester A mixture of 6-isopropyl-3-methoxycarbonyl oxaazulanone (2.63 g) morpholine (1.87 g) and (8) (4.60 g) in EtOH (40 ml) was stirred under reflux for 12 hr, the solvent was evaporated. The residue was diluted with ether, the solution was washed with water and brine, dried over MgSO$_4$, and concentrated in vacuo. The residue was chromatographed on SiO$_2$. Elution with n-hexane-ethyl acetate (8:1) gave 3.7 g of (9)

$^1$H-NMR δ (CDCl$_3$) 1.00, 1.07 (3H,d), 1.31, 1.40 (6H,d), 1.17~2.07 (9H,m), 3.02(2H,t), 2.83~3.97 (5H,m), 3.91 (3H,s), 4.54 (1H, b.s), 7.20~7.46 (2H,m), 8.11 (1H,s), 8.26, 8.38 (1H,d), 9.27, 9.39 (1H,d).

(10) 6-Isopropyl-3-[((3S)-methyl-4-hydroxy)-1-butyl]-azulene-1-carboxylic acid methyl ester A solution of (9) (3.4 g) was treated with mixture (AcOH-H$_2$O-THF=3:1:1, 50 ml). After stirring for 10 hr at 25° C., the reaction mixture was concentrated in vacuo. After distillation with toluene azeotropically, the residue was chromatographed on SiO$_2$. Elution with n-hexane-ether (1:1) gave 2.5 g of (10)

$^1$H-NMR δ (CDCl$_3$) 1.00, 1.06 (3H,d, J=6.16 Hz), 1.31, 1.39 (6H,d,J=7.03 Hz), 1.21~2.10 (3H,m), 2.90~3.29 (3H,t+m), 3.50 (2H,t), 3.92 (3H,S), 7.17~7.46 (2H,m), 8.12 (1H,s), 8.25, 8.37 (1H,d,J=10.55 Hz), 9.40, 8.52 (1H,d,J=10.76 Hz).

(11) 6-isopropyl-3-[((3S)-methyl-4-phthalimide)-1-butyl]-azulene-1-carboxylic acid methyl ester A solution of triphenyl phosphine (6.6 g) in THF (90 ml) was added dropwise to a solution of (10) (3.6 g), phthalimide (3.7 g), and diethylazodicarboxylate (4.4 g) in THF (10 ml). After the solution had been stirred at room temperature for 15 hr, the solvent was removed in vacuo. The residue was chromatographed on SiO$_2$. Elution with n-hexane-ethylacetate (4:1) and chloroform gave 4.4 g of (11).

$^1$H-NMR δ (CDCl$_3$) 1.00, 1.06 (3H,d,J=6.16 Hz), 1.30, 1.39 (6H,d,J=7.03 Hz), 1.21~2.10 (3H,m), 2.90~3.29 (3H,t+m), 3.50, 3.60 (2H,d), 3.92 (3H,S), 7.17~7.46 (2H,m), 7.60~7.80 (4H,m), 8.12 (1H,s), 8.25, 8.37 (1H,d,J=10.55 Hz), 9.40, 9.52 (1H,d, J=10.76 Hz).

(12) 6-isopropyl-3-[((3S)-methyl-4-amino)-1-butyl]-azulene-1-carboxylic acid methyl ester The (11) (4.4 g) was treated with hydrazine hydrate (1.24 g) in EtOH (80 ml) under reflux for 2 hr, the solvent was removed in vacuo. The residue was diluted with ethyl acetate and precipitate was filtered off. The organic layers were washed with water and brine, dried over Na$_2$SO$_4$ and concentrated to give 3.0 g of (12).

(13) 6-isopropyl-3-[(3S)-methyl-4-(4-chlorobenzenesulfonylamino)-1-butyl]-azulene-1-carboxylic acid methyl ester A solution of (12) (3.0 g) in acetone (40 ml) was added 5% NaHCO$_3$ aqueous solution (20 ml) and p-chlorobenzenesulfonylchloride (2.5 g), and the mixture was stirred at 0° C. for 30 min, the solvent was removed in vacuo. The residue was extracted with ethyl acetate. The combined ethyl acetate extracts were washed with water and brine, dried over MgSO$_4$, and concentrated in vacuo. The residue was chromatographed on SiO$_2$. Elution with n-hexane-ethylacetate (3:1) gave 4.3 g of (13).

¹H-NMR δ (CDCl₃) 0.94, 1.00 (3H,d,J=5.93 Hz), 1.32, 1.40 (6H,d,J=6.81 Hz), 1.48~1.84 (3H,m), 2.40~3.26 (5H,m), 3.90 (3H,S), 4.71 (1H, b.t), 7.38~7.81 (6H,g+m), 8.04 (1H,s), 8.20, 8.32 (1H,d,J=10.3 Hz), 9.39, 9.51 (1H,d,J=10.76 Hz)

(14) 6-Isopropyl-3-[((3s)methyl-4-(4-chlorobenzenesulfonylamino)-1-butyl]-azulene-1-carboxylic acid.

10% NaOH aqueous solution was added to stirred solution of (13) (0.45 g) in MeOH (10 ml) at room temperature, and the mixture was stirred under reflux for 2 hr, the solvent was removed under reduced pressure. The pH was adjusted to 2-3 with 10% HCl aqueous solution, and the solution was extracted with ethyl acetate. The ethyl acetate extracts were washed with water and brine, dried over MgSO₄ and concentrated in vacuo. The residue was chromatographed on SiO₂. Elution with n-hexano-ethyl acetate (1:1) gave 0.31 g of (14). m.p. 163°~164° C.

¹H-NMR δ (D6-DMSO) 0.88, 0.95 (3H,d,J=5.74 Hz), 1.29, 1.36 (6H,d,J=6.81 Hz), 1.08~2.01 (3H,m), 2.58~3.50 (5H,m), 3.30 (1H,b.t), 7:27~7.80 (6H,g+m), 8.36, 8.48 (1H,d,J=10.33 Hz), 9.33, 9.45 (1H,d,J=10.55 Hz), 12.07 (1H,b.s)

EXAMPLE 7

6-isopropyl-3-[(3S)-methyl-4-(4-chlorobenzenesulfonylamino)butyl]-azulene-1-sulfonic acid sodium salt (Compound 61)

(15) 6-Isoropyl-3-[(3S)-methyl-4-(4-chlorobenzenesulfonylamino)-1-butyl]-azulen The (13) (3.6 g) was treated with 100% phosphoric acid. After stirring for 30 min at 120°, the reaction mixture was poured into ice-water and extracted with ethyl acetate. The ethyl acetate solution was washed with water, dried over MgSO₄ and concentrated in vacuo. The residue was chromatographed on SiO₂. Elution with n-hexane-ethylacetate (4:1) gave 2.9 g of (15). m.p. 100°~101° C.

¹H-NMR δ (CDCl₃) 0.92, 0.99 (3H,d,J=6.15 Hz), 1.30, 1.37 (6H,d,J=6.82 Hz), 1.40~1.83 (3H,m), 2.57~3.19 (5H,m), 4.59 (1H,b.t), 6.93, 7.04 (2H,d,J=10.1 Hz ), 7.10~7.83 (2q,6H), 8.00~8.23 (2H,2d).

(16) 6-isopropyl-3-[(3S)-methyl-4-(4-chlorobenzenesulfonylamino)-1-butyl]-azulene-1-sulfonic acid sodium salt.

SO₃.Pyridine complex (3.45 g) was added to a solution of (15) (3.1 g) in benzene (62 ml). The mixture was stirred and heated under reflux for 1 hr, the solvent was removed in vacuo. 28% sodium methoxide (MeOH solution) was added to a solution of crude product in MeOH (31 ml) and mixture was stirred for 15 hr at room temperature. The solvent was removed in vacuo. The residue was diluted with water, and extracted with THF, dried over Na₂SO₄ and concentrated in vacuo. The residue was chromatographed on SiO₂. Elution with CHCl₃-MeOH (7:1) gave 2.04 g of (16).

m.p. 237°~238° (decomp.)

¹H-NMR δ (D6-DMSO) 0:87, 0.93 (3H,d,J=5.28 Hz), 1.26, 1.34 (6H,d,J=6.81 Hz), 1.40~1.90 (3H,m), 2.58~3.15 (5H,m), 3.30 (1H,b.s), 6.98~7.25 (2H,m), 7.50~7.92 (5H,q+s) 8.14, 8.26 (1H,d,J=10.11 Hz), 8.87, 8.99 (1H,d,J=10.54 Hz).

EXAMPLE 8

6-isopropyl-3-[4-(benzenesulfonylamino)-cis-2-butenyl]-azulene-1-carboxylic acid (Compound 68)

(1) 2-Butyne-1,4-diol-mono-t-butyldimethylsilyl ether

Sodium hydride (4.65 g) was washed with pentane, and suspended in THF (100 ml). A solition of 2-butyne-1,4-diol (10.0 g) in THF (50 ml) was added to the suspension, and the mixture was stirred at 0° for 30 min. Then, the t-butyl dimethyl silyl chloride (17.5 g) was added into the solution, and the whole mixture was stirred for 2 hr. The reaction was quenched by the addition of saturated aqueous NH₄Cl, followed by extraction with ether. The combined ether extracts were washed with water and brine, dried over MgSO₄ and concentrated in vacuo. The residue was chromatographed on SiO₂. Elution with n-hexane-ether (1:1) gave 18.4 g of (1).

¹H-NMR δ (CDCl₃) 0.06 (6H,s), 0.85 (9H,s), 1.76 (1H,t), 4.10~4.35 (4H, d,d).

(2) 4-Bromo-2-butyn-1-ol t-butyldimethylsilylether

Triphenylphosphine (7.87 g) and carbon tetrabromide (9.95 g) were added to a stirred solution of (1) (5.0 g) in CH₂Cl₂ (50 ml) at −25≈°, and the mixture was stirred at the same temperaturre for 15 min. The reaction was quenched by the addition of saturated aqueous, NaHCO₃, followed by extraction with ether. The combined ether extracts were washed with brine, dried over MgSO₄ and concentrated in vacuo. The residue was chromatographed on SiO₂. Elution with n-hexane gave 6.58 g of (2).

¹H-NMR δ (CDCl₃) 0.05 (6H,s), 0.83 (9H,S), 3.85 (2H,t), 4.28 (2H,t).

(3) 2-(5-t-Butyldimethylsilyloxy-3-pentane)-malonic acid dimethyl ester

Sodium hydride (4.76 g) was washed with pentane, and suspended in THF (47.6 ml). A solution of dimethyl malonate (18.1 g) in THF (150 ml) was added to the suspension, and the mixture was stirred at 0° for 20 min. Then, (2) (24.0 g) of HMPA (100 ml) was added into the solution, and the whole mixture was stirred for 1 hr. The reaction was quenched by the addition of saturated aqueous NH₄Cl, followed by extraction with ether. The combined ether extracts were washed with water and brine, dried over MgSO₄ and concentrated in vacuo. The residue was chromatographed on SiO₂. Elution with n-hexane-ether (4:1) gave 22.0 g of (3).

¹H-NMR δ (CDCl₃) 0.10 (6H,s), 0.90 (9H,s), 2.71~2.89 (2H,d.t), 3.58 (1H,t), 3.74 (6H,s), 4.25 (2H,t).

(4) 6-t-Butyldimethylsilylory-4-hexynecarboxylic acid methl ester

A solution of (3) (22.0 g) in DMSO (50.0 ml) and water (1.8 ml) was mixed with NaCl (4.51 g). After stirring at 130°~140° for 12 hr, the reaction mixture was poured into ice-water and extracted with ether. The ether extracts were washed with water and brine, dried over MgSO₄ and concentrated in vacuo. The residue was chromatographed on SiO₂. Elution with n-hexane-ether (2:1) gave 11.0 g of (4).

¹H-NMR δ (CDCl₃) 0.10 (6H,s), 0.91 (9H,s), 2.53 (3H,s), 3.70 (3H,s), 4.28 (2H,s).

(5) 6-t-Butyldimethylsilyloxy-4-hexyne-1-ol

Diisobutylaluminium hydride (1.0M solution in hexane, 78.1 ml) was added to a stirred solution of the (4) (10.0 g) in toluene (80 ml) at −78°, and mixture was stirred at −78° for 30 min and 0° for 30 min. The reaction was quenched by the addition of MeOH. After dilution with ether, brine was added. The mixture was stirred at room temperature until the organic layer became clear. The aqueous layer was extracted with ether. The combined ether extracts were dried over MgSO₄ and concentrated in vacuo. The residue was chromatographed on SiO₂. Elution with n-hexane-ether (1:1) gave 8.03 g of (5).

$^1$H-NMR δ (CDCl₃) 0.06 (6H,s), 0.85 (9H,s), 1.32~1.85 (2H,m), 1.85 (1H, b.s.), 2.12~2.31 (2H,d.t), 4.22 (2H,t).

(6) 6-t-Butyldimethylsilyloxy-4-cis-hexene-1-ol

To a solution (5) (3.50 g) in acetone (35.0 ml) was added (methyl-benzoate) chromium tricarbonyl (0.84 g). This mixture was transferred to an autoclave and stirred at 120° C. for 12 hr under 70 kg/cm² H₂ pressure. The reaction mixture was cooled to room temperature and removed from the autoclave. The mixture was stirred for 1 hr at room temperature, and the solvent was removed in vacuo. The residue was chromatographed on SiO₂. Elution with n-hexane-ether (3:2) gave 2.10 g of (6).

$^1$H-NMR δ (CDCl₃) 0.08 (6H,S), 0.90 (9H,S), 1.50~1.80 (2H,m), 1.83~2.32 (2H,m), 2.01 (1H,b.s), 3.61 (2H,b.t), 4.17, 4.22 (2H,d), 5.23~5.64 (2H, 2d,t).

(7) 6-t-Butyldimethylsilyloxy-cis-4-hexenal

AcONa (0.044 g) and PCC (0.649 g) were added to a solution of (6) (0.23 g) in CH₂Cl₂ (10 ml) at 0° C., and mixture was stirred for 2 hr. After dilution with ether, the reaction mixture was filtered through a SiO₂ column. The filtrate was concentrated to give 0.22 g of (7)

$^1$H-NMR δ (CDCl₃) 0.08 (6H,s), 0.90 (9H,s), 2.20~2.60 (4H,m), 4.20, 4.27 (2H,d), 5.18~5.71 (2H,2d,t), 9.78 (1H,t).

The compound 54–59, 62–66 are obtained in the same manner as the methods of Example 6 and the compounds 67 and 69 are obtained in the same methods as Example 7 and 8 respectively.

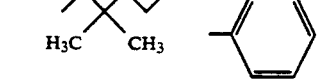

| Compound | R | X | R₁ | m.p. (°C.) |
|---|---|---|---|---|
| 54 | COOH | CH₃ (dashed) chain | phenyl | 84–86 |
| 55 | COOH | CH₃ (wedge) chain | phenyl | 100–101 |

-continued

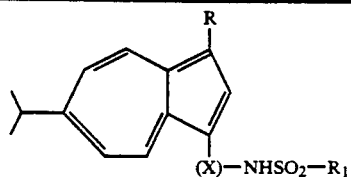

| Compound | R | X | R₁ | m.p. (°C.) |
|---|---|---|---|---|
| 56 | COOH | CH₃ (dashed) chain | phenyl | 85–88 |
| 57 | COOH | CH₃ (wedge) chain | phenyl | 155–156 |
| 58 | COOH | CH₃ (dashed) chain | phenyl | 91–93 |
| 59 | COOH | CH₃ (wedge) chain | phenyl | 88–89 |
| 60 | COOH | CH₃ (wedge) chain | 4-Cl-phenyl | 163–164 |
| 61 | SO₃Na | CH₃ (wedge) chain | 4-Cl-phenyl | 237–238 |
| 62 | COOH | chain (dashed) | phenyl | 122–124 |
| 63 | COOH | chain (wedge CH₃) | phenyl | 123–125 |
| 64 | COOH | H₃C, CH₃ gem-dimethyl | phenyl | 73–75 |
| 65 | COOH | CH₃, CH₃ gem-dimethyl | phenyl | 180–182 |
| 66 | COOH | CH₃, CH₃ gem-dimethyl | 4-Cl-phenyl | 209–210 |
| 67 | SO₃Na | CH₃, CH₃ gem-dimethyl | 4-Cl-phenyl | 190–191 |

-continued

| Compound | R | X | $R_1$ | m.p. (°C.) |
|---|---|---|---|---|
| 68 | COOH | (trans -CH=CH-CH2-) | phenyl | 170–171 |
| 69 | COOH | (cis -CH=CH-CH2-) | phenyl | 180–181 |

Structure: azulene with isopropyl group, R at one position, and (X)—NHSO$_2$—R$_1$ substituent.

What is claimed is:

1. A compound of the formula:

(azulene structure with $R_2$, $R_1$, and Y—N(R$_3$)—A—B substituents)

wherein:
$R_1$ is —SO$_3$H;
$R_2$ is H or a lower alkyl group;
$R_3$ is H, a lower alkyl or benzyl group;
Y is a straight-chain or branched-chain alkylene group of $C_{1\sim10}$ or an alkenylene group of $C_{2\sim6}$;
A is —SO$_2$—;
B is a phenyl, lower-alkylphenyl, lower-alkyloxyphenyl, nitrophenyl, trifluoroalkylphenyl, mono- or di-halogenophenyl, naphthyl or tetrahydronaphthyl group and pharmaceutically acceptable alkali-addition salts thereof.

2. A compound of the formula:

(azulene structure with SO$_3$H, $R_2$, and Y—NH—SO$_2$—B substituents)

wherein:
$R_2$ is a hydrogen atom or lower alkyl group;
B is a phenyl, lower alkylphenyl, lower alkyloxyphenyl, nitrophenyl, trifluoromethylphenyl, mono- or di-halogenophenyl, naphthyl or tetrahydronaphthyl group;
Y is a straight-chain or branched-chain alkylene group of $C_{1\sim10}$ or a alkenylene group of $C_{2\sim6}$.
And pharmaceutically acceptable alkali-addition salts thereof.

3. A compound of the formula:

(azulene structure with $R_1$, $R_2$, and Y—NH—SO$_2$—B substituents)

wherein:
$R_1$ is —SO$_3$H;
$R_2$ is a lower alkyl group;
B is phenyl or halogenophenyl;
Y is a straight-chain or branched-chain alkylene group of $C_{3\sim6}$ or an alkenylene group of $C_{3\sim5}$, and pharmaceutically acceptable alkali-additon salts thereof.

4. A therapeutic composition containing such an amount of a compound as defined in claim 1 as is effective as a thromboxane A$_2$ and a prostaglandin endperoxide receptor antagonist, in combination with a pharmaceutically acceptable carrier.

* * * * *